(12) United States Patent
Nagaoka et al.

(10) Patent No.: US 6,518,249 B1
(45) Date of Patent: Feb. 11, 2003

(54) OLIGOSACCHARIDE DERIVATIVES AND PROCESS FOR PRODUCING THE SAME

(75) Inventors: Masato Nagaoka, Tokyo (JP); Hideyuki Shibata, Tokyo (JP); Itsuko Kimura, Tokyo (JP); Shusuke Hashimoto, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 09/485,978

(22) PCT Filed: Aug. 21, 1998

(86) PCT No.: PCT/JP98/03703

§ 371 (c)(1), (2), (4) Date: Feb. 18, 2000

(87) PCT Pub. No.: WO99/10360

PCT Pub. Date: Mar. 4, 1999

(30) Foreign Application Priority Data

Aug. 22, 1997 (JP) ............................................. 9-240298

(51) Int. Cl.[7] ........................ A61K 31/70; C07H 17/02
(52) U.S. Cl. ........................................ 514/25; 536/17.9
(58) Field of Search ............................ 536/17.9; 514/25

(56) References Cited

U.S. PATENT DOCUMENTS 5,698,534 A 12/1997 Nagaoka et al. .............. 514/54
5,891,862 A * 4/1999 Mandeville, III et al. ..... 514/54

FOREIGN PATENT DOCUMENTS

EP 0 612 527 A 8/1994
EP 0 645 143 A 3/1995

* cited by examiner

Primary Examiner—Kathleen K. Fonda
(74) Attorney, Agent, or Firm—Frishauf, Holtz, Goodman & Chick, P.C.

(57) ABSTRACT

An oligosaccharide derivative, at higher homogeneity than fucose polysaccharide and rhamnose polysaccharide and with greater antiulcer effects, which is represented by the following general formula:

$$Y-OCH(CH_2NHR)_2$$

wherein Y represents an oligofucose or oligorhamnose at a polymerization number of 2 to 20, where the hydroxyl groups may or may not be partially modified in the form of sulfate ester, and R represents phenyl group, a higher alkylphenyl group, a higher alkyl group or $-(CH_2)_n-NHX$ wherein n is an integer of 1 to 10 and X represents a higher alkanoyl group or an alkylamino group.

13 Claims, 3 Drawing Sheets

OLIGOSACCHARIDE DERIVATIVES AND PROCESS FOR PRODUCING THE SAME

This application is the U.S. national stage entry under 35 U.S.C. §371 of PCT/JP98/03703, filed Aug. 21, 1998.

FIELD OF THE INVENTION

The present invention relates to an oligosaccharide derivative and a process for producing the same. More specifically, the invention relates to an oligofucose or oligorhamnose derivative, which is effective for prevention and treatment of inflammation and ulceration on the mucosa of gastric organs such as stomach and duodenum.

BACKGROUND OF THE INVENTION

Conventional antiulcer agents include those for controlling gastric juice secretion, such as $H_2$-blockers and proton pump inhibitors. For the purpose of active therapeutic treatment of gastritis and gastric mucosal cells, use of prostaglandins or basic fibroblast growth factors have recently been studied. These pharmaceutical agents, on the one hand, exert efficacious therapeutic effects. On the other hand, however, these pharmaceutical agents potentially cause the onset of ulcer, specifically the recurrence of ulcer, for which a specific bacterial species Helicobacter pylori is responsible. Therefore, it is remarked that gastric ulcers should essentially be treated, including the disinfection of the bacterial species (Masahiro Asaka, "Helicobacter pylon and disorders of gastric mucosal membrane", Sentan-Igaku-Sha (Top Medicine Press), Jul. 1, 1995).

It has aaditionally been known that microbial cells of certain species of Bifidobacteria or lactic acid bacteria and polysaccharides or oligosaccharides prepared from these microbial cells, Phaeophyceae Chordariales nemacystus or green laver (Monostroma nitidum) are effective in not only the prevention of ulceration but also in the promotion of the healing thereof, and thus are useful as antiulcer agents (JP-A-6-247861; JP-A-7-138166) . These polysaccharides and oligosaccharides primarily comprise fucose and/or rhamnose. Specifically, fucoidan, a fucose polymer, exerts effects to prevent ulcer formation and to promote the healing of urceration and additionally exerts an action to inhibit the adhesion of H. pylori. Nevertheless, these polysaccharides and oligosaccharides per se are not satisfactory in terms of their antiulcer activity. Furthermore, it is difficult to recover these polysaccharides and oligosaccharides at homogenous states including the homogeneity of their molecular weights.

SUMMARY OF THE INVENTION

It is a primary object of the invention to provide an oligosaccharide derivative having higher homogeneity and greater antiulcer effects than those of the aforementioned conventional polysaccharides, and another object of the present invention is to provide a process for producing the same.

According to an embodiment of the present invention, there is provided an oligosaccharide derivative represented by the following general formula:

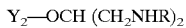

wherein, $Y_1$ represents an oligofucose at a polymerization number of 2 to 20, where the hydroxyl groups may or may not be partially modified in the form of sulfate ester, and R represents phenyl group, a higher alkylphenyl group, a higher alkyl group or —$(CH_2)_n$—NHX wherein n is an integer of 1 to 10 and X represents a higher alkanoyl group or an alkylamino group with or without substituents.

According to another embodiment of the present invention, there is also provided an oligosaccharide derivative represented by the following general formula:

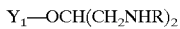

wherein, $Y_2$ represents an oligorhamnose at a polymerization number of 2 to 20, where the hydroxyl groups may or may not be partially modified in the form of sulfate ester, and R represents phenyl group, a higher alkylphenyl group, a higher alkyl group or —$(CH_2)_n$—NHX wherein n is an integer of 1 to 10 and X represents a higher alkanoyl group or an alkylamino group with or without substituents.

These oligosaccharide derivatives have various properties including excellent antiulcer effect.

The present invention also provides a process for producing an oligosaccharide derivative comprising the steps of converting the sugar residue at the reducing end of the oligofucose or oligorhamnose to aldehyde group through oxidative degradation, generating a Schiff base by allowing the aldehyde group to react with at least one of corresponding alkylamines and allylamines, and reducing the Schiff base to obtain an oligosaccharide derivative.

That is, in the process according to the present invention, fucoidan (fucose polysaccharide) or rhamnan (rhamnose polysaccharide) is modified into an oligosaccharide (an oligomer comprising about 3 to 20 molecules of fucose or rhamnose) through acid treatment, and then, the oligosaccharide is subjected to oxidation with periodate, reaction with corresponding amines, and reductive treatment According to another aspect of the invention, there is provided an inhibitor for H. pylori which comprises the oligosaccharide derivative, namely oligofucose derivative and/or oligorhamnose derivative according to the present invention.

According to still another aspect of the present invention, there is provided an agent for preventing and therapeutically treatment of gastric ulcer, said agent comprising the oligosaccharide derivative, namely oligofucose derivative and/ or oligorhamnose derivative according to the present invention.

According to one embodiment of the present invention, the process for producing an oligosaccharide derivative comprises the following steps 1 to 8.

Step 1: Using known extraction methods, polysaccharides are extracted from marine algae (such as Phaeophyceae Chordariales nemacystus, Hydrilla, Fucus, and Monostroma nitidum) containing fucoidan, rhamnan or rhamnan sulfate.

Step 2: The recovered polysaccharides are dissolved in a solution of hydrochloric acid or trifluoroacetate of about 0.075 N to 0.1 N; the mixture is heated at 100° C. for 10 to 20 minutes, to modify the polysaccharides into the form of oligosaccharides. After the treatment, the resulting reaction mixture is neutralized with sodium hydroxide, followed by addition of $NaBH_4$ to the neutraized mixture for reductive treatment at ambient temperature or 4° C. for 16 hours.

Step 3: The solution of the oligosaccharides in the alditol form as recovered by the procedures of the step 2 is desalted by dialysis (a fractionating molecular weight of 500) or electro-dialysis or by using an ion exchange resin.

Step 4: To the solution recovered at the step 3, sodium metaperiodate is added for reaction in a vessel immersed in an ice bath for about one hour. Herein, an oligosaccharide in a structure such that sugars except the sugars at the reducing ends or the non-reducing ends are never oxidized, for example (1→3)

oligosaccharide, may satisfactorily be subjected to the reaction for a longer period of time. Ethylene glycol at a volume excessive to periodic acid is added to the reaction solution, for additional reaction for about one hour. The resulting solution is subjected to desalting in the same manner as in the step 3. By the procedure, an oligosaccharide derivative (in liquid) with an aldehyde group at the end can be recovered.

Step 5: Acetic acid is added to the solution from the step 4 to a final concentration of 0.5 M, which is subjected to reaction at ambient temperature for 20 hours. The reaction solution is dialyzed against a dialysis membrane of a fractionating molecular weight of 500; the inner dialysis residue solution is freeze-dried to recover an objective oligosaccharide. Additionally, the oligosaccharide fraction can be desalted by dialysis. Alternatively, the oligosaccharide fraction can be fractionated and desalted by chromatography on an active-charcoal column and gel filtration to prepare a fraction of an appropriate molecular weight.

Step 6: The oligosaccharide fraction recovered at the step 5 is dissolved in an aqueous solution containing 40% to 50% propanol, followed by addition of allylamines or alkylamines, for reaction at 45° C. for 2 hours, to prepare a Schiff base. In this case, any substance (dimethyl sulfoxide, dimethylformamide, etc.) capable of dissolving oligosaccharides and alkylamines may satisfactorily be used as the solvent. Then, any alkylamine and any allylamine may satisfactorily be selected, with no specific limitation, for use in the reaction; preference is given to anilines with or without substituents and higher alkylamines with or without substituents, wherein the substituents include for example alkyl groups, alkanoylamino groups and alkylamino groups.

Step 7: Volan trimethylamine is added to the solution recovered at the step 6, to reduce the Schiff base at 45° C. for 20 hours. Reducing agents satisfying the purpose (for example, Volan dimethylamine, $NaCNBH_4$, $NaBH_4$, etc.), in addition to Volan trimethylamine, can be used appropriately.

Step 8: After the termination of the reduction at the step 7, the solvent is distilled off by means of an evaporator and the like; by subsequently partitioning the resulting solution in a mixture solution of chloroform:methanol:water=2:1:1, the resulting aqueous phase is collected. By rinsing the aqueous phase in chloroform and freeze-drying the aqueous phase, an oligosaccharide derivative comprising an oligosaccharide-alkylamine complex can be recovered. Depending on the properties of the alkylamine, appropriate solvents may be selected and used for the partition and extraction.

It is verified that the oligosaccharide derivative according to the present invention exerts the effect to inhibit the adhesion of *H. pylori* as a causative bacterial species of gastric ulcer and the effect to therapeutically treat ulcer induced by acetic acid.

According to the present invention, the pharmaceutical agent for preventing and therapeutically treatment of gastric ulcer can be prepared in pharmaceutical dosage forms appropriately selected, which can be administered at an amount appropriately selected. Generally, however, the pharmaceutical agent is blended with a pharmaceutically acceptable carrier in liquid or solid, followed by addition of solvents, dispersants, emulsifiers, buffers, stabilizers, excipients, binders, disintegrators, and lubricants and the like, and the resulting mixture is formulated as tablets, granules, powders, powdery formulations, capsules and the like for use. The dose of the pharmaceutical agent appropriately ranges from about 0.1 to 10 mg/kg, preferably from 0.3 to 3 mg/kg, for most adults per day.

BEST MODE FOR CARRYING OUT THE INVENTION

EXAMPLE 1

(Production of Oligofucose Derivative)

Figure 1:
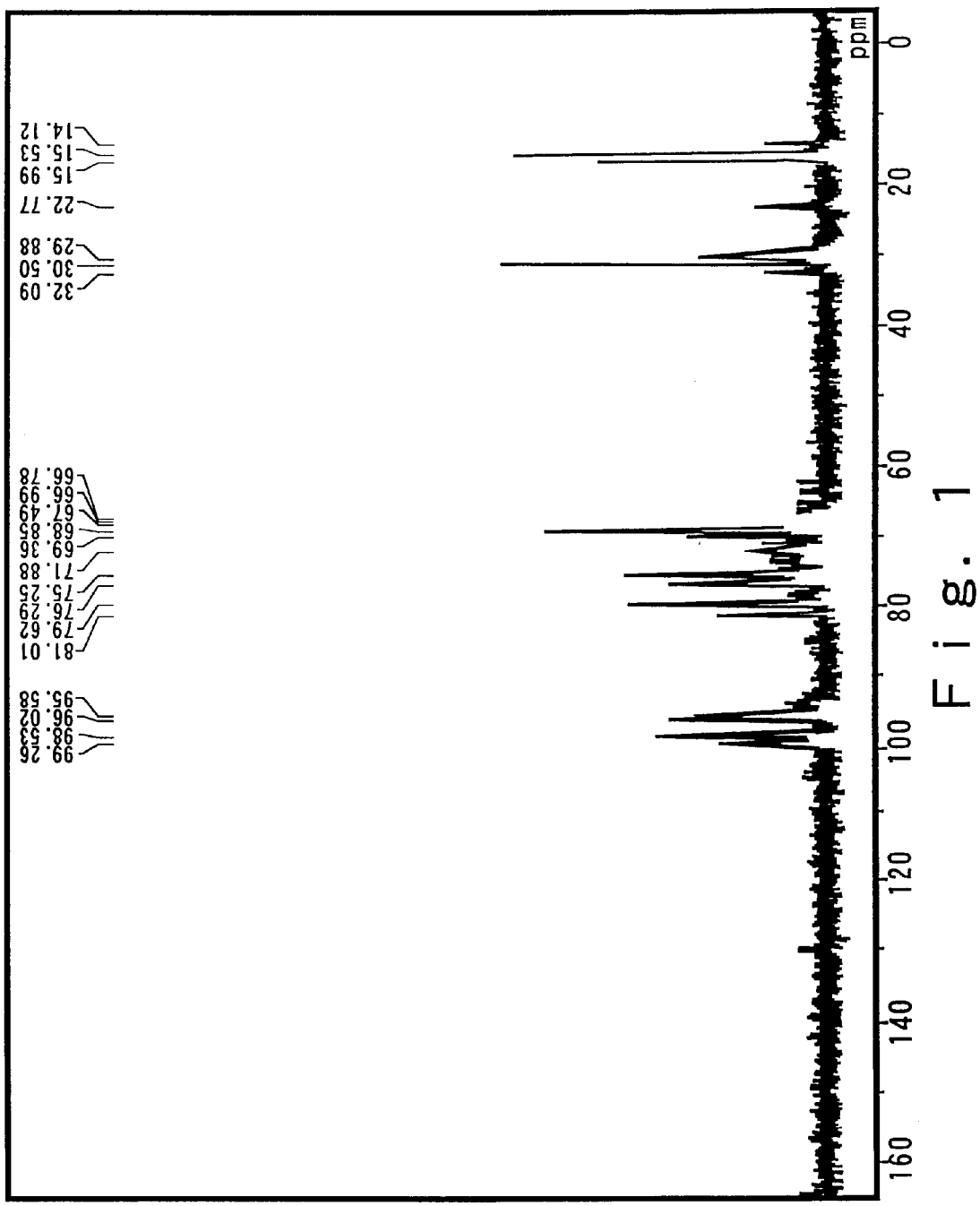
FIG. 1 shows $^{13}$C-NMR chart of oligofucose dodecylaniline derivative (OFDAD)

(1-1) Extraction of Fucoidan and Preparation of Fucose Oligosaccharide

*Cladosiphon okamuranus* Tokida desalted in deionized water was suspended at a ratio of 1 kg of the algae per one liter of deionized water. Using hydrochloric acid, the suspension was adjusted to pH 2. The resulting suspension was heated and extracted at 100° C. for 10 minutes, to filter and recover the algae through gauze; the filtrate was centrifuged at 9,000 rpm for 60 minutes to discard the insoluble matters.

The resulting supernatant was neutralized by using NaOH, followed by addition of sodium metaperiodate to a final concentration of 0.2 M, to decompose contaminated alginic acid and subsequent reaction in darkness for 20 hours; and then, ethylene glycol was added to the reaction mixture to terminate the reaction. Sodium borohydride was added to the resulting solution to a final concentration of 0.2 M, for reaction at ambient temperature for 16 hours. The solution was concentrated by ultrafiltration (fractionating molecular weight of 5,000) and subsequently dialyzed. Using hydrochloric acid, the inner dialysis residue solution was adjusted to pH 2 and treated under heating at 100° C. for 10 minutes. The resulting solution was dialyzed and freeze-dried, to recover fucoidan (4 g/1 kg of wet algae).

The fucoidan was dissolved to a final concentration of 200 mg/mL, followed by addition of hydrochloric acid (or trifluoroacetic acid) to a final concentration of 0.075 to 0.1 M. The resulting mixture was heated at 100° C. for 10 minutes and then cooled to ambient temperature. The solution was neutralized with NaOH, followed by addition of $NaBH_4$ at a ratio of 200 mg per one gram of fucoidan, for reaction at 4° C. for 20 hours. The reaction solution was adjusted to pH 6 by using acetic acid and desalted by an electro-dialysis apparatus (Microacilyzer™ with a membrane AC220; manufactured by Asahi Chemicals, Co.). After desalting, $NaIO_4$ was added to the sample solution to a final concentration of 0.2 M, for reaction in a vessel immersed in an ice bath for one hour. Ethylene glycol of a quantity corresponding to 2 equivalents of periodate was added to the reaction solution, for subsequent reaction in the vessel immersed in the ice bath for one hour. The reaction solution was dialyzed through a dialysis membrane with a fractionating molecular weight of 500 (manufactured by Spectrum Co.); the resulting inner dialysis residue solution was freeze-dried, to recover an oligosaccharide sample (with an average molecular weight of about 1,000 to 3,000 or an average polymerization degree of 8 to 14).

(1-2) Oxidation of Fucose Oligosaccharide with Periodic Acid $NaIO_4$ was added to 100 mL of 2% solution of a fucose oligosaccharide to a final concentration of 0.2 M, for reaction in the vessel immersed in the ice bath for one hour. An equal volume of ethylene glycol was added to the reaction solution, for reaction in the vessel immersed in the ice bath for one hour. The resulting reaction solution was charged into a 500-mL column packed with active charcoal (active charcoal for chromatography; manufactured by Wako Pure Chemicals, Co., Ltd.); and then, non-adsorbed matters were eluted in 3 liters of water. 3 liters of 35% ethanol were added into the column, to recover the adsorbed fraction. The fraction was concentrated with an evaporator, to recover an oligosaccharide of aldehyde form (at a yield of about 25%).

(1-3) Reaction with Amines and Reduction

Figure 2:
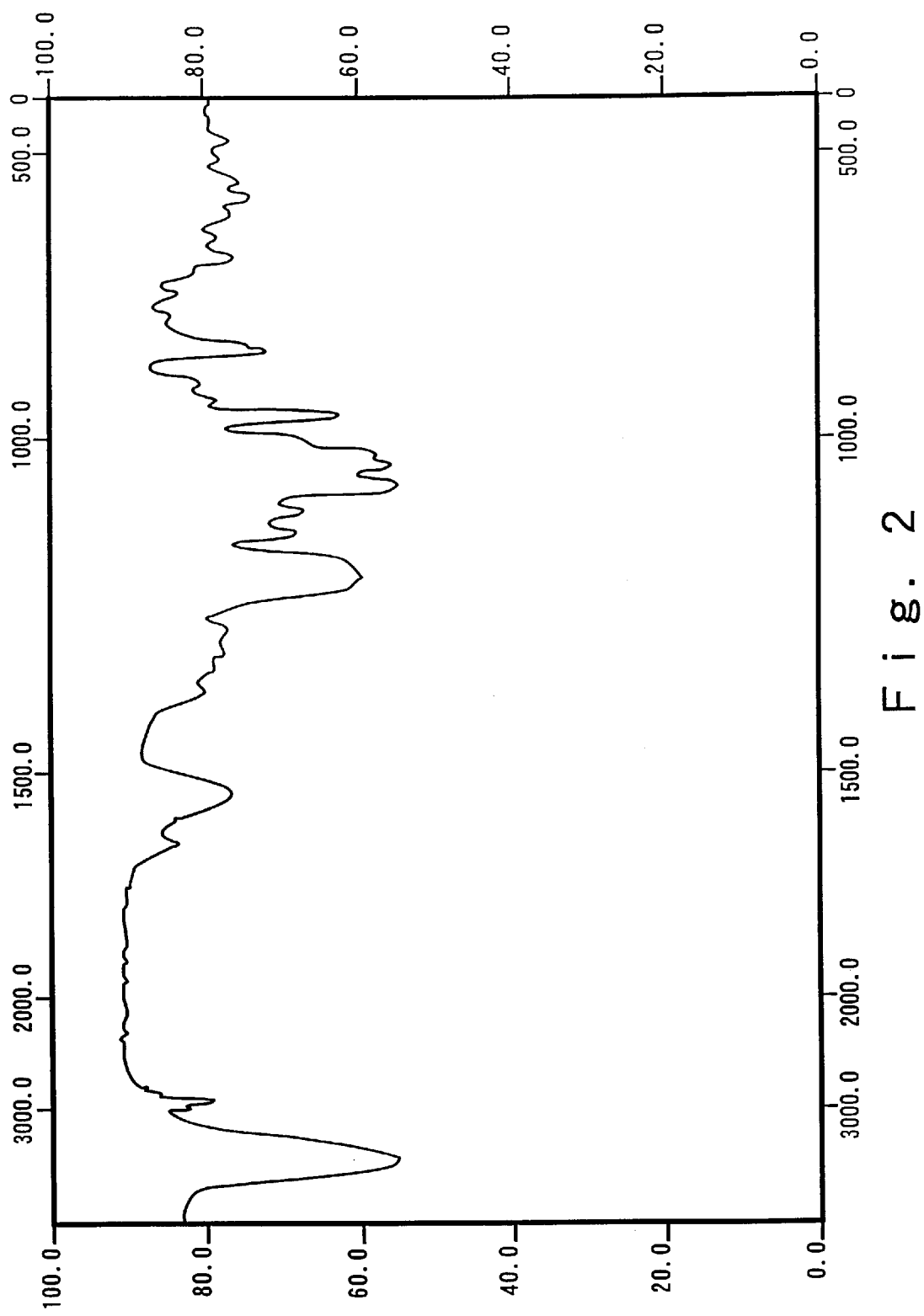
FIG. 2 shows IR chart of oligofucose dodecylaniline derivative (OFDAD)

The aldehyde derivative of the oligosaccharide as produced above in (1-2) was dissolved in 50% n-propanol water to a final ratio of 50 mg/mL, followed by addition of dodecylaniline at a ratio of 10 mg/mL, for subsequent reaction at 45° C. for 2 hours; and to the resulting reaction mixture was thereafter added a Volan dimethylamine complex to a final concentration of 10 mg/mL for 20-hr reaction at 45° C. The resulting reaction solution was dried into solid under reduced pressure. After subsequently adding to the resulting solid residue a mixture solution of chloroform:methanol:water=2:1:1, the resulting aqueous phase was collected, to which an equal volume of chloroform was added for separation and rinsing. The procedure was repeated two times. The resulting aqueous phase was freeze-dried, to recover oligofucose dodecylaniline derivative, OFDAD (at a yield of about 64%). The structure of the derivative was determined as the following formula 1 on the basis of the analytical results by methylation analysis and NMR. Furthermore, the hydroxyl groups at position 4 in the fucose residues are partially modified as sulfate ester. FIG. 1 shows a $^{13}$C-NMR chart of oligofucose dodecylaniline derivative, OFDAD, and FIG. 2 an IR chart of oligofucose dodecylaniline derivative, OFDAD.

(1)

OFDAD

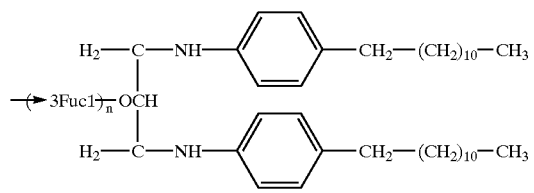

Instead of dodecylaniline, alkylamines such as hexylaniline, aniline or laurylamine were used for the similar reaction as in (1-3); the reaction solution was similarly separated to recover oligofucose derivatives such as oligofucose hexylaniline derivative (OFDAD) of the formula 2, oligofucose aniline derivative (OFAN) of the formula 3, and oligofucose laurylamine derivative (OF-LA) of the formula 4.

(2)

OFHAD

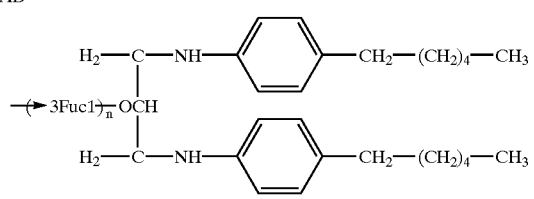

(3)

OFAN

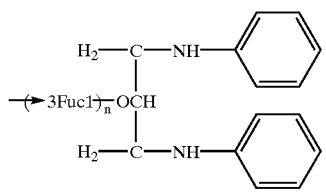

(4)

OF-LA

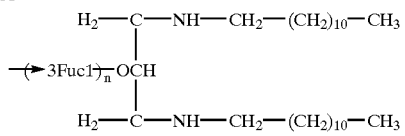

EXAMPLE 2

(Production of Oligorhamnose Derivative)

(2-1) Production of Rhamnose Oligosaccharide

Dried algae of green laver (*Monostroma nitidum*) was suspended in water of a 10-fold volume and heated at 100° C. for 2 hours to immerse rhamnan sulfate. The resulting solution was centrifuged to discard solid matters, followed by addition of ethanol to precipitate and collect polysaccharides, which were then dissolved in water; the resulting solution was subjected to dialysis to remove low-molecular components; rhamnan sulfate was recovered in the resulting inner dialysis residue solution. Subsequently, hydrochloric acid was added to the inner dialysis residue solution containing rhamnan sulfate to a final concentration of 0.01 N, and the resulting mixture was heated at 100° C. to induce desulfuration. Thereafter, the resulting solution was dialyzed again, to recover rhamnan in the inner dialysis residue solution.

In the similar manner as for fucoidan described above, the rhamnan was subjected to decomposition with weak acids, reduction, and periodate oxidation, to recover an aldehyde-form oligosaccharide derivative (with an average molecular weight of about 1,000 to 1,500).

(2-2) Reaction with Amine Derivative

The fraction was conjugated to dodecylaniline in the same manner as described above, to recover oligorhamnose dodecylaniline derivative (OR-DA) of the formula 5 (at a yield of about 10%).

(5)

OR-DA

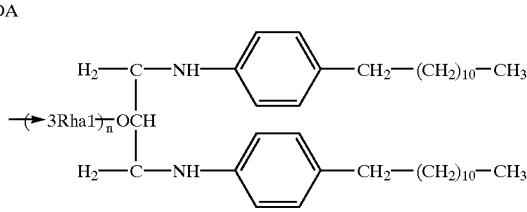

Other than derivatives of the formulas 1 to 5 as produced above in Examples 1 and 2, derivatives were produced by the aforementioned process, as listed in the following formulas 6 to 10.

OF-DP

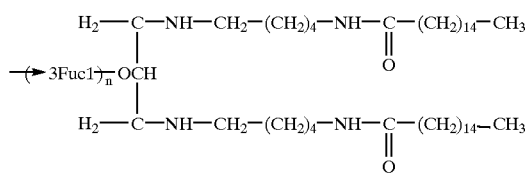

(6)

OFAC

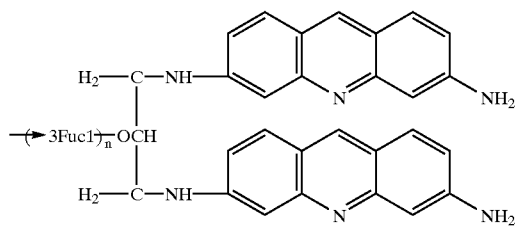

(7)

OFACP

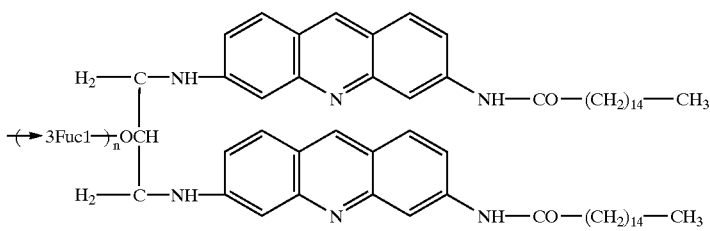

(8)

OFDAODA

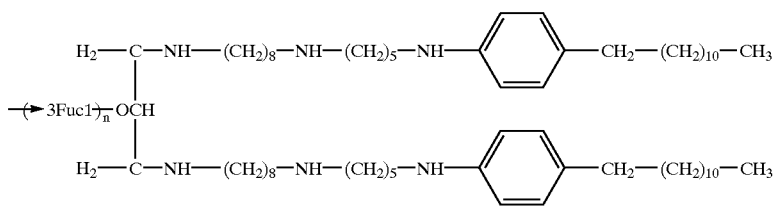

(9)

OFDAOACF

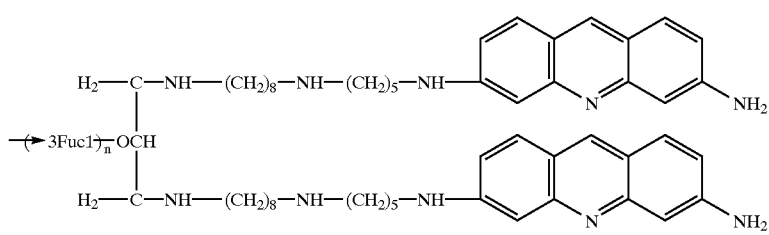

(10)

EXAMPLE 3
(Antiulcer Action Test 1)

Figure 3:
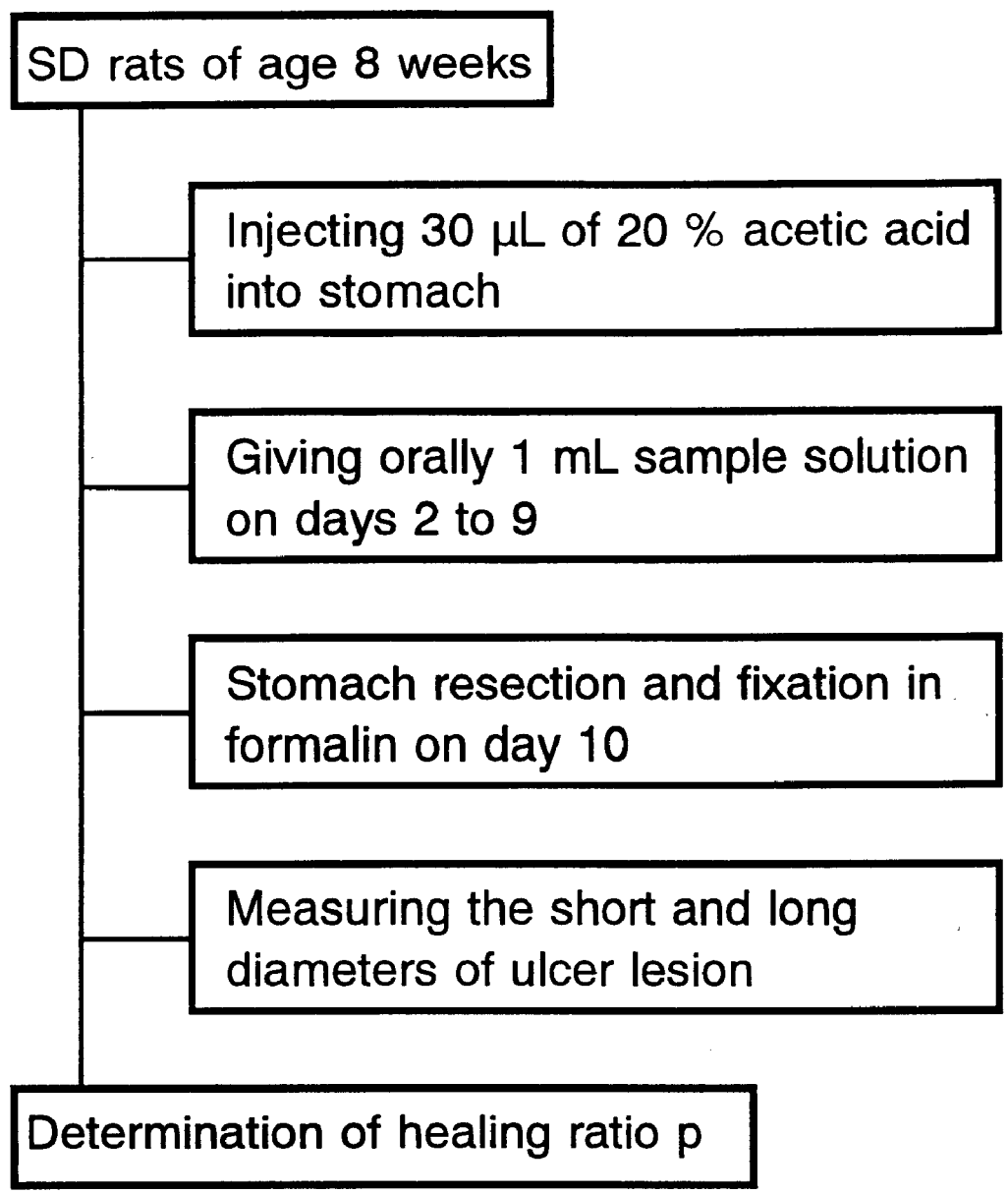
FIG. 3 shows a flow chart of the procedures to induce ulcer with acetic acid.

The antiulcer action of the oligofucose dodecylaniline recovered in Example 1 for acetate-induced ulcer was tested. FIG. 3 shows a flow chart of the procedures to induce ulcer with acetic acid. Experiments and efficacy determination were carried out as shown in FIG. 3. 30 μL of 20% acetic acid was directly injected in the stomachs of 8-week-old SD rats on day 1; on days 2 to 9, 1 mL of the sample solution was orally administered once daily to these rats. During the test term, feeds and water were fed ad libitum.

After final dosage, these rats were starved; from these rats were resected the stomachs, which were fixed in formalin. Ulcer index was determined by measuring the short diameter and long diameter of each ulcer lesion, to examine the healing ratio. When an effect was observed at a 5-% level of significance or less ($p \leq 0.05$), compared with a control group, the effect was determined as significant. Herein, the healing ratio in % was determined as follows:

$$\text{healing ratio } (\%) = 1 - \frac{\text{area of ulcer in a test group}}{\text{area of ulcer in control group}} \times 100$$

The results are shown below in Table 1.

TABLE 1

|  | Ulcer index (mean ± SD) | Healing ratio (%) |
| --- | --- | --- |
| Control group (11) | 11.3 ± 2.6 | — |
| Test group 0.1 mg/rat/day × 8 (10) | 6.2 ± 1.5* | 45.0 |
| Test group 0.5 mg/rat/day × 8 (10) | 8.2 ± 4.7* | 27.8 |
| Test group 1.0 mg/rat/day × 8 (10) | 6.7 ± 2.9* | 41.4 |

*) $p \leq 0.05$ compared with control group.

EXAMPLE 4
(Antiulcer Action Test 2)

The similar test of antiulcer action was conducted by using the oligofucose alkylamine derivatives recovered in Example 1 in place of the test solution above. More specifically, oligofucose hexylaniline and oligofucose laurylamine were used as the sample solutions, for the same procedures as in Example 3, to examine the effects of oligofucose hexylaniline and oligofucose laurylamine against acetate-induced ulcer.

The results are shown below in Tables 2 and 3.

TABLE 2

|  | Ulcer index (mean ± SD) | Healing ratio (%) |
| --- | --- | --- |
| Control group (10) | 11.6 ± 4.3 | — |
| Test group 0.1 mg/rat/day × 8 (10) | 7.5 ± 2.8* | 35.5 |
| Test group 0.3 mg/rat/day × 8 (10) | 8.4 ± 3.8* | 27.5 |
| Test group 1.0 mg/rat/day × 8 (10) | 7.8 ± 2.8* | 33.5 |

*) $p \leq 0.05$ compared with control group.

TABLE 3

|  | Ulcer index (mean ± SD) | Healing ratio (%) |
| --- | --- | --- |
| Control group | 10.3 ± 3.8 | — |
| Test group 0.5 mg/rat/day × 8 (7) | 5.1 ± 2.1* | 50.4 |
| Test group 2.0 mg/rat/day × 8 (10) | 7.2 ± 3.6* | 30.3 |
| Test group 5.0 mg/rat/day × 5 (10) | 9.9 ± 4.8* | 4.6 |

*) $p \leq 0.05$ compared with control group.

EXAMPLE 5
(Antiulcer Action Test 3)

So as to examine the effect of oligofucose dodecylaniline to prevent the ulcer induced by NSAIDS and the like, the action thereof was examined to test the effect to prevent indomethacin-induced disorders.

As to the specific procedures thereof, oligofucose dodecylaniline dissolved in 1 mL of a 0.5-% carboxymethyl cellulose solution was orally given to rats fasted for 18 hours (feeds) and 2 hours (water). Only the carboxymethyl cellulose solution was given to a control group. 2 hours after the sample dosing, 1 mL of 50 mg/mL indomethacin was administered to these rats, to induce damages on the gastric mucosa. 2 hours after the damage induction, the stomachs were resected from these rats, which were fixed in formalin, to measure the length and width of a lesion with damage (bleeding lesion) and determine the area, thereby calculating the suppression ratio of the occurrence of damage. Thus, the effect of oligofucose dodecylaniline to prevent indomethacin-induced gastric damage was evaluated. The results are shown below in Table 4.

TABLE 4

|  | Ulcer index (mean ± SD) | Healing ratio (%) |
| --- | --- | --- |
| Control group | 46.06 ± 24.72 | — |
| Test group 0.5 mg/rat/day × 8 (7) | 25.33 ± 14.57* | 45.0 |
| Test group 2.0 mg/rat/day × 8 (10) | 19.23 ± 14.67* | 58.2 |
| Test group 5.0 mg/rat/day × 8 (10) | 4.29 ± 4.48* | 90.7 |

*) $p \leq 0.05$ compared with control group.

EXAMPLE 6
(Examination of Effects to Inhibit the Adhesion of *H. pylori* and to Inhibit the Proliferation)

*H. pylori* has been attracting attention in recent years as a causative bacterial species for gastric ulcer. It is suggested that because the frequency of the relapse of gastric ulcer is high in patients infected with the bacterial species but low in the patients treated at a disinfectant process of the bacterial species by using high doses of antibiotics, the disinfection of the bacterial species or the prophylaxis of the infection with the bacterial species is significantly important in terms of the prevention of the relapse of gastric ulcer. In a practical sense, therapeutic guidelines of ulcer in European countries and USA list the disinfection of the bacterial species; in Japan, also, an effect on the bacterial species will be demanded for a therapeutic agent of ulcer from now on, because the ratio of the infection with the bacterial species increases in the course of aging.

The bacterial species can be disinfected effectively by the therapeutic treatment with a high dose of antibiotics and proton pump inhibitors in combination, but it is considered that another therapeutic treatment is essentially developed from the respect of the emergence of resistant bacteria. As to the mechanism of the infection with the bacterial species, the bacterial species transfers from the gastric mucosal layer via flagellum motion to gastric epidermal cells, where the bacterium specifically recognizes and adheres to the fucose residue of the Louise b-type (Leb) sugar chains on the gastric epidermal cells. A report tells that sialic acid, sulfatide and laminin are involved in the adhesion of the bacterium, but fucose is considered to function as a significant recognition site for the specific adhesion on gastric epidermal cells.

It is indicated that fucoidan derived from *Phaeophyceae Chordariales nemacystus* not only exerts the antiulcer effects but also inhibits the process of the adhesion. Because it was predicted that the oligosaccharide alkylamine derivative could serve for the prevention of the infection of *H. pylori* and the relapse of gastric ulcer in addition to the promotion of ulcer healing, if the oligosaccharide alkylamine derivative could inhibit the adhesion of *H. pylori*, the effect thereof on the inhibition of the adhesion was examined. Furthermore, the effect thereof on the inhibition of the proliferation was also examined.

As to the specific procedures, the reducing end of a Leb-type sugar chain was oxidized with periodate, to prepare an oligosaccharide with the resulting oxidative end according to the method by P. W. Tang, et al. (Biochem. Biophys. Res. Commun., Vol. 132, 1985, pp. 474–480). The oligosaccharide was conjugated with diaminohexane and subsequently fixed on a microplate (Covalink Plate™;

manufactured by NUNC Co.) for use in fixing amino groups. On the plate was placed biotin-labeled *H. pylori,* for reaction at ambient temperature for one hour. Then, oligofucose dodecylaniline derivative was allowed to be appropriately present concomitantly. The reaction solution was rinsed in a buffer to remove never adhering bacteria.

Subsequently, 100 μL of a 50 μg/mL streptoavidin solution was added to each well, for reaction at ambient temperature for one hour, whereby streptoavidin selectively bound to the bacterium remaining in the wells. Excess streptoavidin was removed by rinsing. Then, 100 μL of a peroxidase-labeled biotin solution of 2.5 μg/mL was added to each well. After reaction at ambient temperature for 30 minutes, excess of the enzyme labeled biotin was removed. By the procedures, the enzyme-labeled biotin selectively bound to the biotinylated bacterium. The enzyme activity was detected and assayed, by adding 100 μL of a substrate solution (ABTS peroxidase substrate system; manufactured by KPL Co.) for 10-min reaction. The assay was conducted by measuring the absorbance at a wave length of 405 nm. Because the measured absorbance indicates the quantity of the bacterium recognizing and binding to the Leb-type sugar chain, the ratio of the decrement of the absorbance due to the addition of oligofucose dodecylaniline indicates the ratio of the adhesion inhibition.

At the co-presence of the oligofucose dodecylaniline derivative within a range of 10 to 100 μg/mL, the increase of the added oligofucose dodecylaniline derivative decreases the absorbance as shown below in Table 5 depicting the results of the inhibition activity of the oligofucose dodecylaniline derivative on the adhesion of *H. pylori* to the Leb-type sugar chain. Thus, it is indicated that the binding between *H. pylori* and the Leb-type sugar chain is inhibited by oligofucose dodecylaniline derivative.

TABLE 5

| Sample concentration (μg/mL) | Absorbance (at 405 nm) |
|---|---|
| 0 | 1.015 |
| 10 | 0.855 |
| 100 | 0.486 |
| 1000 | 0.080 |

Subsequently, the effect of oligofucose dodecylaniline on the inhibition of the proliferation of *H. pylori* was examined. A clinical isolate strain *H. pylori* 6-34 ($1.5 \times 10^8$ CFU/mL) cultured in a brucella culture medium containing 0.1% β-cyclodextrin was suspended at a volume of 100 μL in 1 mL of the same culture medium, followed by addition of 10 μL of the sample (oligofucose dodecylaniline) solution, for culturing for 72 hours. The effect was judged as follows; based on the turbidity (OD 600 nm) of the sample solution to the turbidity of the control group, the ratio of proliferation inhibition was determined by the following formula. Consequently, the ratio of proliferation inhibition was 71.8%.

$$\text{Proliferation inhibition ratio (\%)} = 1 - \frac{\text{turbidity of sample solution}}{\text{turbidity of control group}} \times 100$$

As has been described above, in accordance with the present invention, there is provided a pharmaceutical agent having an action to promote ulcer healing and an action to inhibit the adhesion of *H. pylori* and being effective for the prophylaxis and therapeutic treatment of gastric mucosal inflammation potentially progressing to ulcer or cancer. A very low dose of the aforementioned substance exerts a healing effect for gastric ulcer and an effect to prevent mucosal damage; and additionally, the substance can readily be prepared as an oligosaccharide more homogenous than polysaccharides in terms of physico-chemical properties and activity. Hence, the substance can readily be used as a pharmaceutical agent.

We claim:

1. An oligofucose derivative chosen among the group consisting of the following formulae:

OFDAD

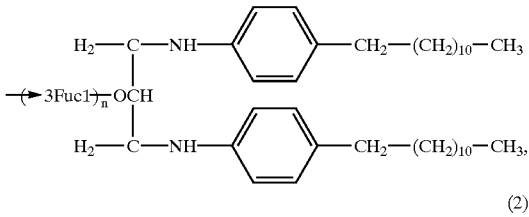

(1)

OFHAD

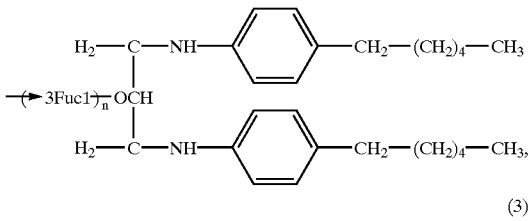

(2)

OFAN

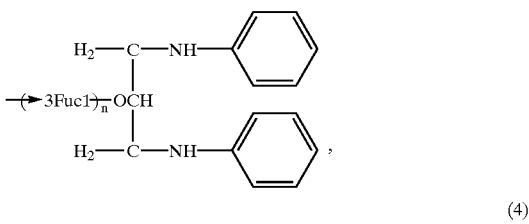

(3)

OF-LA

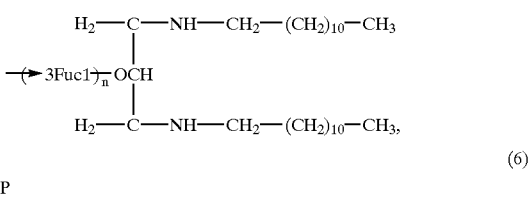

(4)

OF-DP

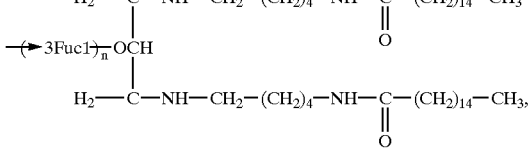

(6)

OFAC

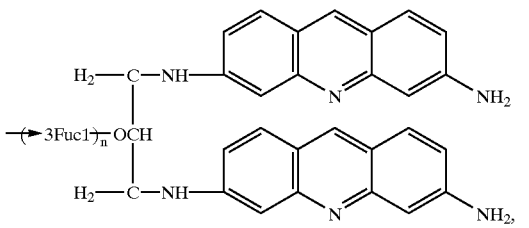

(7)

-continued

OFACP (8)

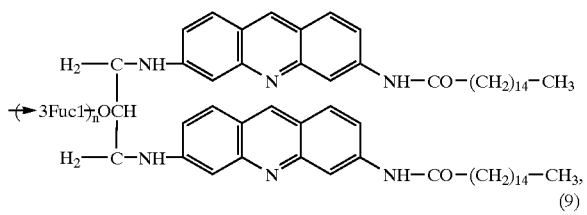

OFDAODA (9)

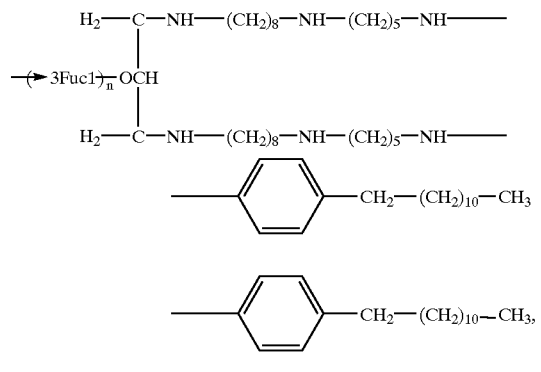

and (10)

OFDAOACF

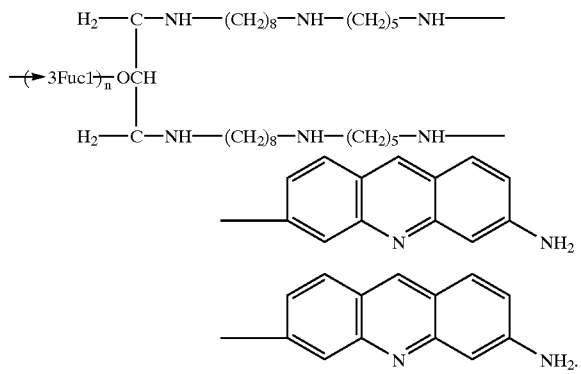

2. An inhibitor for *Helicobacter pylori,* containing an effective amount of an oligofucose derivative according to claim 1 in a pharmaceutically acceptable carrier.

3. A prophylactic or therapeutically treating agent for gastric ulcer, containing an effective amount of an oligofucose derivative according to claim 1 in a pharmaceutically acceptable carrier.

4. A process for producing an oligofucose derivative as defined in claim 1, comprising the steps of:

converting a sugar residue at the reducing end of an oligofucose to an aldehyde group through oxidative degradation;

generating a Schiff base by reacting the aldehyde group with at least one of a corresponding alkylamine and allylamine; and reducing the Schiff base to obtain the oligofucose derivative.

5. An oligofucose derivative as claimed in claim 1 designated OFDAD.

6. An oligofucose derivative as claimed in claim 1 designated OFDAD.

7. An oligofucose derivative as claimed in claim 1 designated OFAN.

8. An oligofucose derivative as claimed in claim 1 designated OF-LA.

9. An oligofucose derivative as claimed in claim 1 designated OF-DP.

10. An oligofucose derivative as claimed in claim 1 designated OFAC.

11. An oligofucose derivative as claimed in claim 1 designated OFACP.

12. An oligofucose derivative as claimed in claim 1 designated OFDAODA.

13. An oligofucose derivative as claimed in claim 1 designated OFDAOACF.

* * * * *